United States Patent [19]

Whistler

[11] Patent Number: 4,601,211

[45] Date of Patent: Jul. 22, 1986

[54] MULTI-PORT VALVE IN A GAS COLLECTION SYSTEM AND METHOD OF USING SAME

[75] Inventor: Wayne J. Whistler, Glendora, Calif.

[73] Assignee: The Perkin-Elmer Corporation, Norwalk, Conn.

[21] Appl. No.: 680,689

[22] Filed: Dec. 12, 1984

[51] Int. Cl.$^4$ .................. G01N 1/26; G01N 1/24; G01N 1/20; G01N 1/14

[52] U.S. Cl. .................. 73/863.33; 73/863.56; 137/554

[58] Field of Search ........... 73/863.31, 863.33, 863.56; 137/554

[56] References Cited

U.S. PATENT DOCUMENTS 4,113,434  9/1978  Tanaka et al. .............. 73/863.56
4,156,437  5/1979  Chivens et al. .............. 137/554

Primary Examiner—Stewart J. Levy
Assistant Examiner—Tom Noland
Attorney, Agent, or Firm—Randall G. Wick; Thomas P. Murphy; Edwin T. Grimes

[57] ABSTRACT

A multi-port valve uses a flexible sample tube to selectively intercept gases flowing from inlet ports into a common manifold space. The manifold space is placed under sufficient vacuum to insure that gas samples will be selectively received by the sample tube when the sample tube is placed in close proximity to the selected inlet port to be sampled. The sample tube is arranged so that gases to be sampled from the selected port wash over the entrance end of the sample tube so that contaminated or mixed gases from the manifold space are prevented from entering the sample tube. The sample tube is mounted to pivot inside a valve body and is moved by a sample tube guide which rotates inside the valve body to selectively align the sample tube with the inlet ports. The valve body may be sealed by a cover through which the valve guide is driven to rotate by a magnetic coupling, or by a bearing seal through which the sample tube guide projects. The sample guide may be rotated in a stepwise fashion by a stepper motor for slow collection rates, or may be rotated quickly by a motor for rapid sampling. Magnetic detectors or a shaft decoder may be used to monitor the position of the sample tube guide. The multi-port valve may be used in a system in which a measuring device such as a mass spectrometer and a data system are used.

9 Claims, 9 Drawing Figures

MULTI-PORT VALVE IN A GAS COLLECTION SYSTEM AND METHOD OF USING SAME

FIELD OF THE INVENTION

This invention relates generally to the field of multi-port valves for selecting gas samples to be provided to a mass spectrometer, and more particularly relates to such valves which avoid the use of moving mechanical seals by selectively intercepting samples of flowing gas in gas collection systems.

BACKGROUND OF THE INVENTION

A prior computer controllable multi-port valve is described in U.S. Pat. No. 4,156,437 issued on May 29, 1975. The patent lists Clyde C. Chivens and Wayne J. Whistler as inventors and is assigned to The Perkin-Elmer Corporation. The patent shows a rotating selector manifold for selecting between a plurality of input ports to interconnect with an output port. The selector manifold has a conduit for transferring gases and has resilient "O" rings to seal the conduit to the ports. The selector manifold is mounted on a shaft which rotates in a bearing attached to the housing of the multi-port valve. The patent also describes the use of a manifold position indicator to identify the position of the selector manifold.

Many problems are encountered in providing a system to collect and measure the composition of atmospheric gases from a plurality of remote locations using a mass spectrometer. Prior systems have been used to collect gases from remote locations, to pass the gases through a multi-port valve to select gases from a particular location for sampling, and to measure the gases repeatedly in sequence using the mass spectrometer. A multi-port selector valve used in such an application must be rugged in construction and avoid the use of components subject to wear, so as to avoid the need for frequent servicing. Since such gas measurement systems are often used in hospitals for patient monitoring or in industrial plants for environmental safety monitoring, it is very important that selector valves used in such systems operate continuously for long periods of time without failure or need for maintenance. Such selector valves should be inexpensive in construction and avoid the need for complex adjustments or alignment during manufacture or use. It is also important that such valves not produce false measurements when foreign materials, such as liquids exhaled by a medical patient, are mixed with the gases to be sampled. It is also important that the multi-port selector valves avoid contamination of the sample gases by preventing gas leaks into the valves.

Careful attention must be paid to avoid trapped volumes in valve and manifold systems in order not to degrade the rise time of the mass spectrometer sample measurement when gas composition changes occur. Also, it is important to keep the samples from remaining dormant in the line, and to reduce the delay time required to purge out the resident gases from the inlet lines when a sample is to be taken.

OBJECTS OF THE INVENTION

It is therefore an object of the invention to provide a multi-port valve for use in a gas collection system.

Another object of the invention is to provide a multi-port valve which is durable in construction and which avoids excessive wear during use.

A further object of the invention is to provide a multi-port valve which avoids malfunctions when foreign material or debris are present in the gas collection system.

Another object of the invention is to provide a multi-port valve which is inexpensive to construct and which avoids the need for complex or critical adjustments or alignments.

A further object of the invention is to provide a multi-port valve which avoids the use of excessive amounts of electrical power during operation.

Another object of the invention is to provide a multi-port valve which avoids trapped gas volumes in the valve in order to preserve the rise time responsiveness of a mass spectrometer connected to receive gas samples from the valve.

Another object of the invention is to provide a multi-port valve which has a substantially sealed construction to prevent gas from leaking into the valve.

SUMMARY OF THE INVENTION

Briefly described, the present invention is for a selector valve having a flexible sample tube pivotably mounted inside a valve body to move between inlet ports and intercept gases from the inlet ports. A rotating guide is provided to direct the sample tube to each of the inlet ports, in sequence, during operation of the valve. The valve is operated by applying suction to evacuate the valve body and draw gases from the inlet ports into the valve at a relatively high flow rate. Suction is applied to the sample tube in order to selectively obtain gas samples from one inlet port at a time at a relatively low flow rate, without obtaining gas samples which are contaminated with gases mixed from inlet ports other than the inlet port selected. During operation, the sample tube guide is rotated to move the opening of the sample tube into proximity with each of the inlet ports, in sequence, in order to obtain gas samples from the selected inlet ports. The differing rates of gas flow between the selected inlet port and the sample tube is relied on to insure that the sample tube receives gas only from the inlet port selected. That is, no mechanical contact or sealing is used to insure the flow of gas from the selected inlet port to the sample tube. Instead, rapid flushing of gas out of the selected inlet port and past the sample tube opening insures that contamination is prevented from entering the sample tube. The multi-port valve may be equipped with magnetic sensors to detect the position of a magnet on the rotating sample guide in order to detect when the sample tube is properly aligned and in proximity with each of the plurality of input ports. The rotating sample tube guide may be coupled to a stepper motor for movement in increments in a stop-start fashion to each inlet port. Alternatively, the rotating sample tube guide may be spun continuously to move the sample tube past each of the inlet parts rapidly in sequence. The sample tube may be provided with a source of ionizing radiation mounted on the outside of the tube, near its opening in order to ionize the gases surrounding the sample tube. A detector plate and electrometer may be used to sense the presence of ionized gases inside the sample tube and thus detect the blockage of gases through an inlet port. The multi-port valve is particularly adapted for use in a gas collection system in which gases may be rapidly and repeatedly sampled by connecting the selector valve to the input of a gas measurement device, and by decommutating the measurement device output in coordination with the selector valve position.

BRIEF DESCRIPTION OF THE DRAWINGS

The invention is described below in greater detail in conjunction with the drawings wherein.

DETAILED DESCRIPTION

Figure 1:
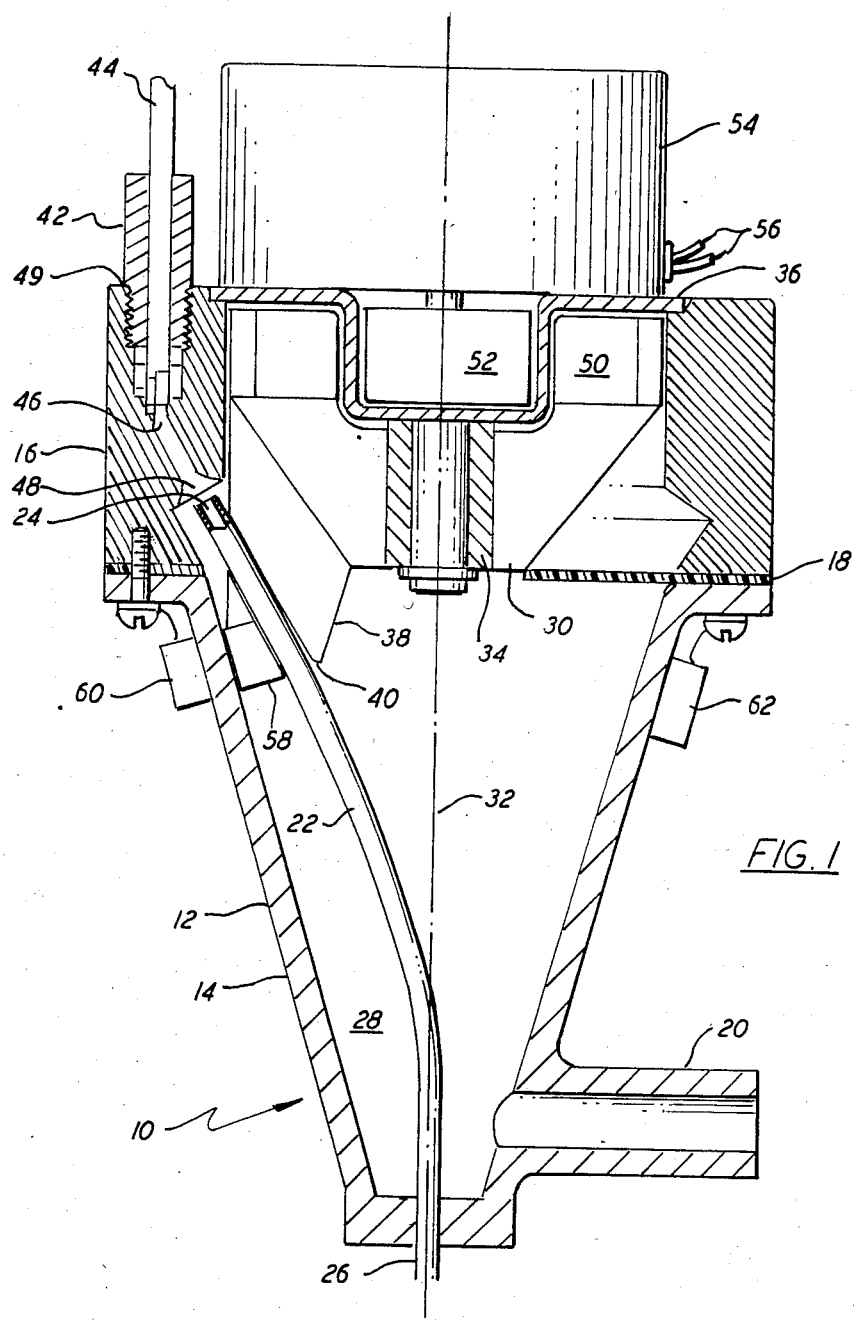
FIG. 1 is a partially cut away, side sectional view of the preferred embodiment multi-port selector valve.

Referring first to FIG. 1, the multi-port valve 10 has a valve body 12 including a vacuum housing 14 and an inlet fitting block 16. The vacuum housing 14 is bolted through an elastomer seal gasket 18 to the inlet fitting block 16 in order to provide an air tight seal and allow for disassembly. The vacuum housing 14 is preferably composed of a non-magnetic, synthetic plastic material such as polycarbonate or the like. The vacuum housing 14 has an outlet port 20 for connection to a vacuum pump (not shown). A sample tube 22 is pivotably mounted inside the vacuum housing 14. It is preferable that the sample tube 22 be composed of Teflon (an E. I. DuPont DeNemours Corporation trademark) brand PTFE material. As an alternative, the sample tube 22 may be composed of a metal material, such as stainless steel, which does not readily absorb gases, thus preventing possible inaccuracies in the measurement of gases to which are susceptible to such absorption. It is preferable that the sample tube 22 be flexible and resistant to fatigue due to bending. The sample tube exit end 26 is rigidly attached to the vacuum housing 14. A sample tube entrance end 24 is open so that gases may be drawn into the tube 22 through the entrance 24.

In operation, the sample tube 22 pivots by bending along its length inside the manifold space 28 inside the vacuum housing 14. The manifold space 28 is a cavity volume inside the valve body 12 having openings through the outlet port 20, the sample tube entrance end 24, and the plurality of inlet ports (as described below). The tube exit end 26 is held in place by the vacuum housing 14 as the tube 22 bends and pivots. The dimensions of the valve 10 may be chosen to accommodate the bending tolerance properties of the material used for the sample tube 22. Lesser degrees of bending should be required for the sample tube 22 if materials having lesser tolerance to bending stresses are used for the tube 22. In operation, a vacuum pump (not shown) is connected to the sample tube exit end 26 to draw gases into the entrance end 24 and through the sample tube 22. The outlet port 20 is pumped with suction to a pressure of approximately 100 to 200 torr.

The multi-port valve 10 has a guide rotor 30 which is mounted for rotation inside the valve body 12. It is preferable that the guide rotor 30 rotate about centerline axis 32 which is aligned with the centerline of the sample tube 22 at the exit end 26 where the sample tube 22 is rigidly attached to the vacuum housing 14. The guide rotor 30 rotates on a bearing 34 which is affixed to a seal cover 36. The seal cover 36 is attached to and makes an airtight seal with the inlet fitting block 16. The guide rotor 30 has a guide arm 38 projecting therefrom. The guide arm 38 is provided with a guide bore 40 there through which has a diameter slightly larger than the diameter of the sample tube 22, so that the sample tube 22 has a loose slip-fit inside the bore 40. The bore 40 is directed and angled to match the shape of the sample tube 22 in natural bending due to the deflection of the tube 22 from its relaxed direction along the axis 32. That is, the bore 40 is shaped so that substantially uniform contact is maintained between the sample tube 22 and the portion of arm 38 inside the bore 40. Such an angle and shape for the bore 40 avoids creating stress concentrations in the tube 22 and avoids binding and excessive wear of the sample tube 22 during operation of the multi-port valve 10. The guide rotor 30 functions as a sample tube guide which is rotated to move the opening end 24 of the sample tube 22 into proximity with each of the inlet ports, as described further below.

The inlet fitting 42 is typical of a plurality of inlet fittings which are threaded into the inlet fitting block 16 in order to provide gases for sampling to the multiport valve 10. The inlet fitting 42 attaches an inlet tube 44 to the block 16 so that gases may flow from the inlet tube 44, and through inlet passage 46 and an expansion passage 48 in the inlet block 16. Taken together, the fitting 42 and passages 46 and 48 form an inlet port 49 which is representative of a plurality (such as eight) such inlet ports of the preferred embodiment selector valve 10. The expansion passage 48 is open to the manifold space 28 and discharges gases into the manifold space 28. The sample tube entrance end 24 is also open to the manifold space 28. Note that the manifold space 28 includes space inside the vacuum housing 14, and the space inside the inlet fitting block 16 which is enclosed by the seal cover 36. Gases are drawn out the outlet port 20 in order to pull gases from the inlet tubes connected to the manifold space 28, and thus prevent gas samples from remaining dormant in the inlet tubes, and to reduce the delay time required to purge out the resident gases from the inlet lines when a sample is to be taken.

The passage 46 and passage 48 are representative of the plurality of passages forming inlet ports in the inlet fitting block 16 for accommodating the plurality of gas inlet tubes connected to the valve 10. The distance between the sample tube entrance end 24 and the expansion passage 48 of the inlet port 49 is preferably large enough to allow the rapid flushing of gases over and past the entrance end 24, and small enough to avoid the flow of gases from the manifold space 28 into the entrance end 24 when the end 24 is proximate and aligned with one of the inlet ports. For the flow rates through the sample tube 22 and inlet ports described herein, the separation distance between the entrance end 24 and the inlet ports (for example, inlet port 49) is nominally 10 to 20 thousanths of an inch. The diameter of the sample tube 22 is made small enough so that misalignments caused by rotational positioning errors of the guide rotor 30 do not prevent the entrance end 24 from intercepting gases flowing from inlet ports. The sample tube 22 is large enough in diameter to insure that sufficient gases are reliably received into entrance end 24. The arm 38 and bore 40 are positioned to direct the sample tube entrance end 24 towards, and align it with, the passage 46 and 48 of the inlet port 49. The entrance end 24 is spaced away from the inlet fitting block 16 when the sample tube 22 is in place inside the guide bore 40 of the guide rotor 30. The distance between the entrance end 24 opening and the block 16 is large enough to allow gas flow from a selected inlet port to wash over the end 24 when the tube 22 is pivoted into alignment with the selected inlet port, such as the inlet port 49. However, the distance between the entrance end 24 and the block 16 is small enough to insure that the entrance end 24 opening receives gases from only the selected inlet port and does not receive mixed or contaminated gases from the manifold space 28. The positioning of the end 24 with respect to the inlet ports, along with the flowing of gases there through provides a valve 10 without the use of moving mechanical seals and avoids trapped volumes which would degrade the rise time responsiveness of measurement devices coupled to receive gases from the tube 22.

In operation, the guide rotor 30 is rotated to pivot the sample tube 22 about the axis 32 to move the sample tube end 24 between the various inlet ports, such as that shown by passages 46 and 48. As the rotor 30 rotates, the sample tube 22 is guided inside the valve 10 by the arm 38 which maintains the tube 22 in a bent position. As the rotor 30 rotates, the tube 22 slips and rotates inside the guide bore 40. The function of the guide rotor 30 is to move the sample tube 22 between each of the inlet ports in order to select the inlet port from which gases are to be drawn into the tube 22. The guide rotor 30 also may be used to hold the tube 22 in alignment with the particular inlet port selected so that only gases flowing from the selected inlet port will enter the tube 22 during a measurement period.

The guide rotor 30 is attached to a magnetic follower 50 to rotate together on the bearing 34. The magnetic follower 50 preferably has a toroidal shape with its axis coincident with the centerline axis 32. The magnetic follower 50 is preferably a multi-pole magnetic follower of conventional construction. The magnetic follower 50 is positioned to rotate about an input rotor 52 which exerts magnetic forces on the follower 50 to cause the follower 50 to rotate as the rotor 52 rotates. The seal cover 36 is formed with a central depression to accommodate the input rotor 52, so that the cover 36 is positioned between the input rotor 52 and the follower 50. The input rotor 52 is mounted on a shaft of a stepper motor 54 which causes the input rotor 52 to rotate on an axis coincident with the centerline axis 32. The stepper motor 54 is a conventional, commercially available component which rotates in stepwise increments in response to electrical signals received on the stepper input wires 56. The follower 50 and rotor 52 are preferably a standard, commercially available magnetic coupling. The function of the follower 50 and rotor 52 is to allow torque to be transmitted from the motor 54 to the guide rotor 30 without a mechanical feed-through in the valve body 12, thus providing a substantially sealed construction using the seal cover 36 to prevent gas from leaking into the valve 10. While a mechanical feed-through, such as a conventional packing gland and rotary seal (not shown), could be used, more torque would be required from motor 54 than is required when follower 50 and rotor 52 are used.

A permanent magnet 58 is attached to the guide arm 38 of rotor 30 and is positioned to rotate inside the manifold space 28 along the inside of the vacuum housing 14. A plurality of magnetic detectors, of which detector 60 and 62 are typical, are mounted around the outside of the vacuum housing 14 in order to sense the location of the permanent magnet 58 and thereby to sense the rotational position of the rotor 30. It is preferable that a magnetic detector be provided corresponding to each gas inlet port so that the magnetic detectors can be used to indicate when the sample tube 22 has been moved into position in alignment with the selected inlet port from which gas is to be drawn by tube 22. It is preferable that the magnetic detectors 60 and 62 be standard, commercially available Hall effect devices which produce an electrical signal upon detection of a magnetic field.

Figure 2:
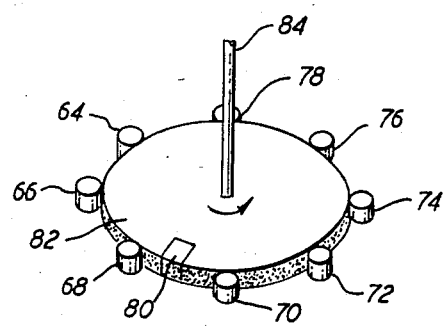
FIG. 2 is a perspective view of a construction analogous to the rotating sample tube guide and magnetic position detectors of FIG. 1.

Referring next to FIG. 2, the operation of the magnetic detectors 60 and 62 and the magnet 58 are portrayed in a simplified pictorial diagram of an analogous construction. The magnetic detectors 64, 66, 68, 70, 72, 74, 76 and 78 correspond to the magnetic detectors exemplified by detectors 60 and 62 in FIG. 1. The magnet 80 corresponds to the permanent magnet 58 of FIG. 1, and is mounted on a rotating disc 82 which is rotated by a shaft 84. The disc 82 corresponds to the guide rotor 30 of FIG. 1. As the shaft 84 turns, the magnet 80 is moved past each of the detectors 64–78 and the detectors 64–78 produce electrical signals in a repeating sequence indicating the rotational position of the disc 82 and magnet 80.

FIG. 2 conceptually illustrates that as the stepper motor 54 of FIG. 1 causes the guide rotor 30 to rotate, magnetic detectors (exemplified by detectors 60 and 62) produce electrical signals to indicate the position of the guide rotor 30 and magnet 58, and thus to indicate the position of the sample tube 22 and to indicate alignment of the sample tube end 24 with inlet ports in the inlet fitting block 16.

Figure 3:
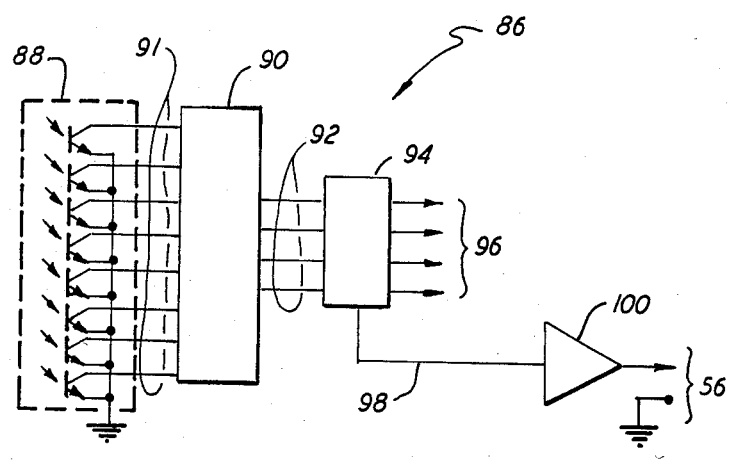
FIG. 3 is an electrical block diagram of circuitry for use with the magnetic position detectors of FIG. 1.

Referring next to FIG. 3, the electronic circuit 86 is used to process electrical signals provided by the position detectors (such as, magnetic detectors 60 and 62) used with the multi-port valve 10 of FIG. 1. The position detectors are represented schematically by the magnetic detector circuitry 88 which includes Hall effect magnetic sensors for each of eight magnetic position detectors used with the multi-port valve 10. The Hall effect sensors of circuit 88 are represented by NPN transistors having their emitters connected together to ground, and their collectors connected as inputs to a converter 90 which preferably is a commercially available binary to binary coded decimal (BCD) converter. Each of the NPN transistors of circuit 88 are Hall effect sensors which allow collector currents to flow in the presence of a magnetic field. The circuit 88 includes eight such transistors with each transistor corresponding to a magnetic detector (such as, detectors 60 and 62) of the multiport valve 10. As illustrated by the analogous construction of FIG. 2, individual ones of the transistors of circuit 88 will turn on to become conductive as the magnet 80 rotates past the corresponding magnetic detectors 64–78.

The binary to BCD convertor 90 receives electrical signals as inputs from the transistor collectors of circuit 88 in a binary format. The purpose of the convertor 90 is to convert the electrical signals from circuit 88 to produce BCD position output signals on the four conductors 92. The BCD signals on the conductors 92 are provided as inputs to a comparator 94. The transistor collector outputs from the magnetic detector circuit 88 are connected to the eight convertor input conductors 91 which are inputs to the convertor 90. The comparator 94 also receives inputs on conductors 96 indicating the desired position for the guide rotor 30 of FIG. 1. That is, electrical signals are provided from an external source such as a control computer (not shown) to the conductors 96 in order to specify the desired rotational position for the rotor 30. The electrical signals on the conductors 96 thus select the position of the sample tube 22 so that gas samples from a selected inlet tube may be obtained.

The comparator 94 produces an electrical signal on a comparator output 98 indicating when the BCD coded signals received on the conductors 92 are equivalent to the BCD coded signals received on the conductors 96. The comparator output 98 is connected as an input to an amplifier 100 which provides electrical signals to the wires 56 for operating the stepper motor 54 (see FIG. 1). The purpose of the comparator 94 and amplifier 100 is to compare the signals on the input lines 92 and 96 and to cause the stepper motor 54 to be actuated and rotate the rotor 30 until the signals on the input conductors 92 are the same as the signals on the conductors 96, and the rotor 30 is rotated to the desired location. That is, when the inputs on the conductors 92 are not equal to the inputs on the conductors 96, the output of the amplifier 100 on the wires 56 is of sufficient voltage to cause the stepper motor 54 to operate and rotate the guide rotor 30. When the inputs on the conductors 92 become equal to the inputs on the conductors 96, the output of the amplifier 100 on the wires 56 becomes zero volts and the stepper motor 54 stops and the guide rotor 30 stops rotating at that point so that gases may be received by the sample tube 22 from the selected inlet port.

Figure 4:
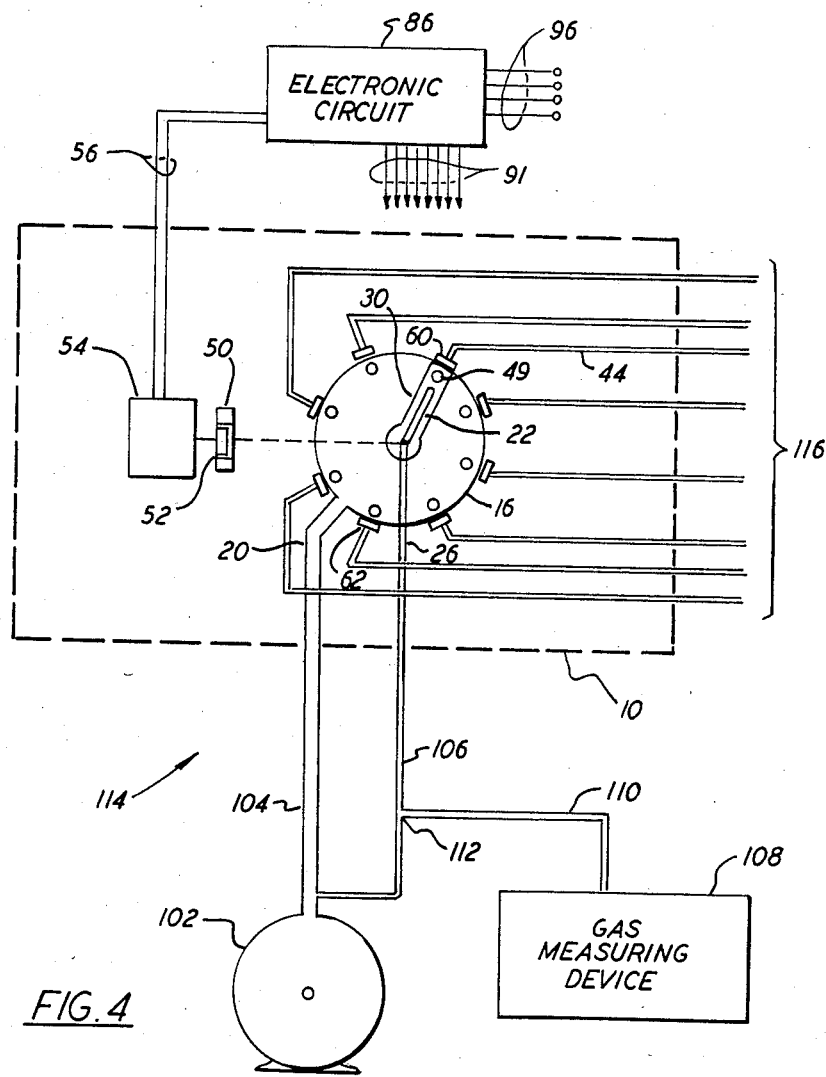
FIG. 4 is a mechanical block diagram of the multi-port selector valve of FIG. 1, further showing the connection of the valve to a vacuum pump.

Referring next to FIG. 4, one application for the multi-port selector valve 10 is shown. The valve 10 is displayed in a symbolic, partially exploded view to more clearly illustrate the operation of the rotor 30 in moving the sample tube 22 to intercept gases from gas inlet ports such as inlet port 49.

The convertor input conductors 91 are connected to the eight magnetic position detectors (exemplified by detectors 60 and 62) arranged around the periphery of the valve 10 to detect the position of the rotor 30.

A standard, commercially available vacuum pump 102 is connected to the pump lines 104 and 106 to pump gases from the outlet port 20 and sample tube exit end 26, respectively. The vacuum pump 102 preferably develops a vacuum of approximately 100 to 200 torr at the output port 20 and preferably obtains a gas volume flow rate through the port 20 and pump line 104 of approximately 33 cubic centimeters per second. The volumetric flow rate for the pump line 104 is set in order to cause a volumetric flow rate through each of the inlet ports (inlet port 49 being typical) of approximately four cubic centimeters per second. The vacuum pump 102 is operated in order to produce a volumetric flow rate through the tube end 26 and pump line 106 of approximately one cubic centimeter per second. As discussed above, the flow rate out through the sample tube 22 is set to be less than the flow rate in through each of the inlet ports in order to insure that contamination free gas samples are obtained by the sample tube 22. The volumetric flow rate in from each inlet port should be approximately a factor of four times as large as the volumetric flow rate out through the sample tube 22.

A gas measuring device 108, such as a mass spectrometer, is connected through a measuring line 110 to a measurement port 112 on the pump line 106. A pressure above approximately 50 torr is produced at the measurement port 112 for introduction to the measuring device 108. The device 108 preferably includes an internal vacuum pump (not shown) for drawing a very small flow of sample gas through the line 110 from the pump line 106 in order to obtain gases from the sample tube 22 for measurement.

The gas flow rate through the pump line 104 is preferably set by a restrictor (not shown) positioned in the line 104 in order to control the flow rate through the line 104. Such a restrictor may include a conventional pressure regulator or a constriction in the pump line 104. The flow rate through the pump line 106 is set by the length and diameter of the tubing used for the pump line 106. The pump line 106 is used as a pressure divider in which the position of the measurement port 112 is set along the length of the pump line 106 in such a location as to receive gases at a pressure intermediate between the pressure inside the manifold space 28 and the pressure produced by the vacuum pump 102. The gas flow rates through the gas inlet tubes 116 are set by the length and diameter of each of the tubes 116 and by the pressure inside the manifold space 28. The vacuum pump 102 is a conventional, oil vane type pump for producing a vacuum pressure of approximately 100 to 200 torr.

Taken together, the apparatus of FIG. 4 forms a gas collection system 114 which includes the multi-port valve 10, the electronic circuit 86, the vacuum pump 102 and the gas measuring device 108. The gas collection system 114 receives input gases to be measured from a plurality of gas inlet tubes 116. The gas inlet tubes 116 are shown as entering the inlet fitting block 16 near each of the corresponding magnetic detectors shown in FIG. 4. Gas inlet tube 44 is typical of the eight gas inlet tubes 116 shown in FIG. 4. The number of gas inlet tubes 116 may be chosen to be larger or smaller than eight in accordance with the particular application for the gas collection system 114.

One typical application for the gas collection system 114 is to collect respiration gases from a plurality of medical patients by connecting the gas inlet 116 to collect gases exhaled by each of the patients. The particular embodiment shown in FIG. 4 would allow the sampling of gases from each of eight different patients. For this application, the stepper motor 54 would be operated to move the guide rotor 30 in a stop-start fashion with stops of approximately 5 seconds duration at each of the gas inlet tubes 116. In this application, the duration for stop or dwell time of the rotor 30 is set to intercept at least one complete breath of respiration from each patient connected to the gas inlet tubes 116. The electronic circuit 86 may also be controlled to skip over stops for gas inlet tubes which are not to be sampled. This allows the system 114 to be used more efficiently by not sampling gases from those of the gas inlet tubes 116 which are not in use. The stepper motor 54 operates so that approximately 100 to 200 milliseconds are required to move the rotor 30 between adjacent inlet tubes entering the inlet fitting block 16.

Figure 5:
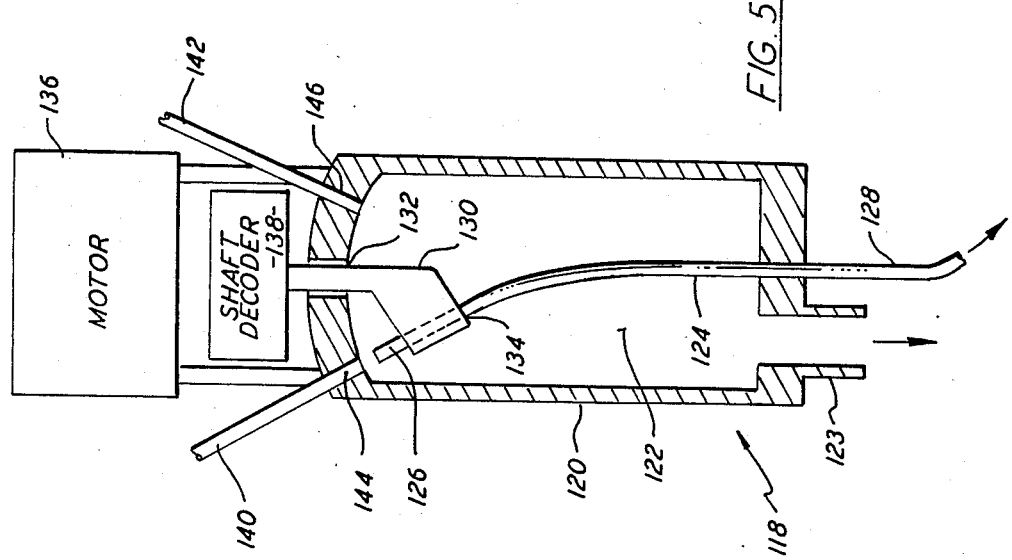
FIG. 5 is a partially cut away, side sectional view of an alternative embodiment multi-port selector valve.

Referring next to FIG. 5, the multi-port valve 118 is an alternative embodiment for the multi-port valve 10 of FIGS. 1-4. The multi-port valve 118 is particularly adapted for applications in which rapid scanning or sampling of a plurality of input gases is required. The valve 118 has a valve body 120 enclosing an inner manifold space 122. The valve body 120 has an outlet port 123 which is connected to a vacuum pump (not shown) for withdrawing gases from inside the manifold space 122. A sample tube 124 is securely attached to the valve body 120 and is positioned to pivot inside the manifold space 122. The sample tube 124 has a sample tube entrance end 126 and a sample tube exit end 128. The exit end 128 is connected to a vacuum pump (not shown) so that sample gases are drawn through the sample tube 124 from inside the manifold space 122.

A guide rotor 130 is mounted for rotation in a gas tight rotary seal 132 in the valve body 120. The seal 132 insures that the valve body 120 has a substantially sealed construction to prevent gas from leaking into the valve 118. The guide rotor 130 has a guide bore 134 through which the sample tube 124 loosely fits. The guide rotor 130 is rotated by an electric motor 136 acting through a shaft decoder 138. The motor 130 is preferably a standard commercially available motor which operates at a substantially constant rotational speed. The shaft decoder 138 has electrical outputs (not shown) which indicate the rotational position of the guide rotor 130. The shaft decoder 138 is preferably a conventional, commercially available shaft decoder used to indicate the rotational position of the guide rotor 130.

Gas sample inlet tubes 140 and 142 are connected to sample tube inlet ports 144 and 146, respectively, to provide gases to be sampled by multi-port valve 118. The sample tube inlet ports 144 and 146 are representative of a plurality of sample tube inlet ports (preferably eight in number) which provide gases into the valve 118.

In operation, a vacuum is provided to the outlet port 123 of approximately 100 to 200 torr in order to produce a gas flow of approximately four cubic centimeters per second from each of the inlet tubes (such as inlet tubes 140 and 142) into the inner manifold space 122. A vacuum of approximately 50 torr is applied to the sample tube exit end 128 in order to produce a gas flow of approximately one cubic centimeter per second through the sample tube 124. The difference in the rate of flow through the inlet ports (for example, ports 144 and 146) and through the sample tube 124 insures that gases flowing from an inlet port into the manifold space 122 will wash over the sample tube entrance end 126 at a high volumetric rate and will insure that the sample tube 124 will intercept gases only from the inlet port selected, and will not receive mixed gases from the manifold space 122. The purpose of the guide rotor 130 is to rotate and pivot the sample tube 124 to align the sample tube 124 with inlet ports (such as ports 144 and 146) to receive sample gases from each of the inlet ports in sequence.

Figure 6:
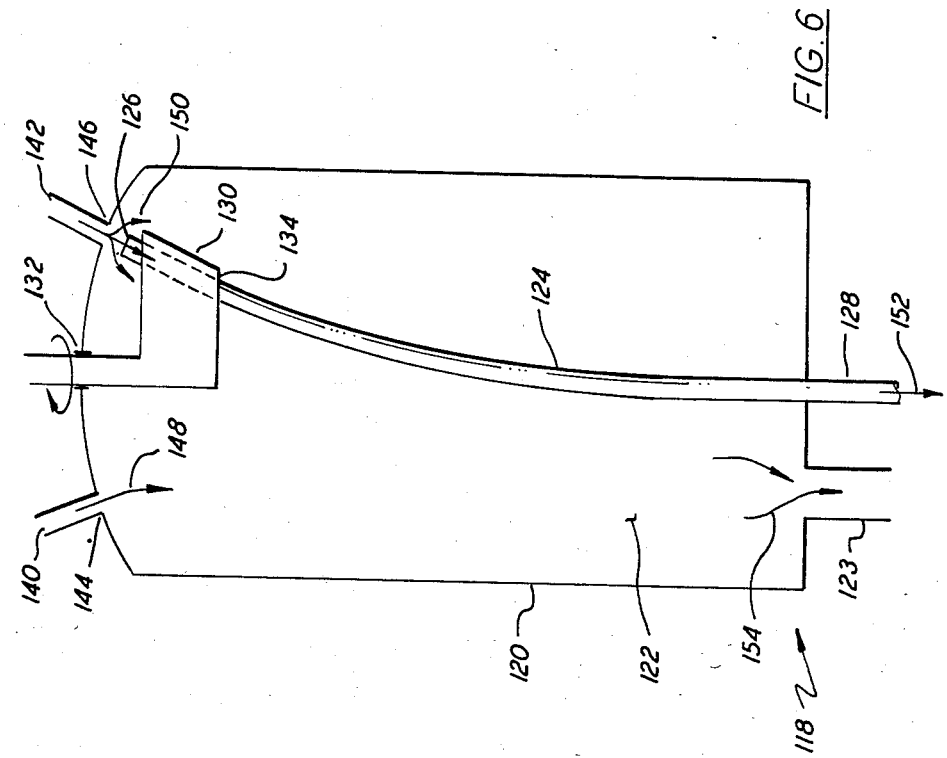
FIG. 6 is a diagram illustrating the flow of gases through the valve of FIG. 5 during normal operations.

Referring next to FIG. 6, the operation of the valve 118 is shown during normal, unobstructed operation. A gas flow 148 of approximately four cubic centimeters per second occurs through the inlet port 144. A gas flow 150 of approximately three cubic centimeters per second flows from the inlet port 146 past the open sample tube entrance end 126 and into the manifold space 122. A gas flow 152 of approximately one cubic centimeter per second is drawn through the sample tube 124 from the sample gases flowing through the inlet port 146. Note that approximately four cubic centimeters per second of gas flows through the inlet passage 146, three cubic centimeters per second of which is in the gas flow 150 traveling past and washing over the tube end 126, and one cubic centimeter per second of which enters the sample tube 124 as the gas flow 152. A gas flow 154 of approximately 31 cubic centimeters per second flows through the outlet port 123. The gas flow rates for the flows 148-154 described herein are given as examples, but are not critical to the operation of the multi-port valve 118. However, it is important that the gas flow rate in through an inlet port (such as the ports 144 and 146) be much higher than the gas flow 152 in order to insure that sufficient gas washes over the tube entrance end 126 to insure that the sample gas flow 52 consists substantially exclusively of gas received from a selected inlet passage port, and that mixed or contaminated gases do not backflow into the tube 124 from the manifold space 122 during the time that a particular inlet port is selected. Thus the differential flow rates between the inlet ports (high flow rates) and the sample tube 124 (a low flow rate) provide valving operation in the valve 118 without the use of mechanical seals and without creating trapped gas volumes.

As the guide rotor 130 is rotated, the sample tube entrance end 126 will move sequentially between the inlet ports and may receive contaminated or mixed gases from the manifold 122 as the rotor 130 moves between adjacent ports. The use of the shaft decoder 138 (see FIG. 5) insures that measurements of contaminated or mixed gases during such between port sampling may be selectively ignored by electronic circuits connected to receive the measurements (see FIG. 8).

Figure 7:
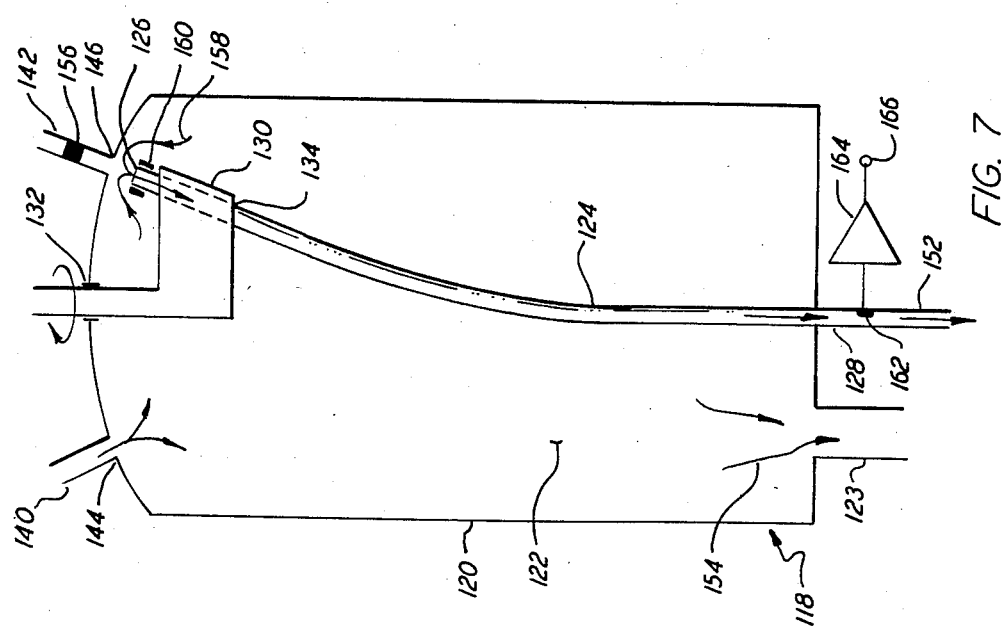
FIG. 7 is a diagram illustrating the flow of gases through the valve of FIG. 5 when gas flow through an inlet port is blocked, and further illustrating an ionization source and an ionized gas detector for sensing the blockage.

Referring next to FIG. 7, the operation of the multi-port valve 118 under abnormal conditions when the inlet tube 142 is plugged by an obstruction blockage 156 is shown. When the inlet tube 142 is blocked, gases cannot flow from the inlet port 146 into the manifold space 122. Such a blockage 156 may be caused by liquids exhaled by a medical patient. When the inlet port 146 is selected by the guide rotor 130, a gas flow 158 of approximately one cubic centimeter per second is drawn from the manifold space 122 into the sample tube entrance end 126. This means that when the input port 146 is selected by the guide rotor 130, the sample gas flow 152 consists of mixed or contaminated gases from the manifold 122 rather than the expected sample gases from the inlet tube 142.

The embodiment shown in FIG. 7 shows the use of an ionizing radiation source ring 160 mounted on the outside of the sample tube 124 near the entrance end 126. The ring 160 projects ionizing radiation into the manifold space 122. The ring 160 is positioned to ionize gases in the manifold 122 but not to ionize gases flowing directly from a selected port into the sample tube entrance end 126. A detector plate 162 is mounted inside the sample tube 124 near the exit end 128 for detecting the presence of ionized gases in the gas flow 152. An electrometer 164 is connected to sense electrical charge on the detector plate 162 and produce an output 166 having a voltage indicating the presence of ionized gases in the gas flow 152.

The function of the ionizing source 160, detector plate 162 and electrometer 164 is to detect and indicate the presence of a blockage (such as blockage 156) in an inlet tube. The electrometer output 166 may be used to indicate when the sample gas flow 152 contains mixed or contaminated gases from the manifold 122 rather than the expected, uncontaminated sample gases from the selected port. Therefore, the electrometer output 166 indicates when the desired gas samples were not received by the sample tube 124 and the gas measurements should be ignored. Use of the ionizing ring 160, plate 162, and electrometer 164 helps to avoid malfunctions in a gas sampling system by signaling when foreign material or debris enter the inlet tubes.

The electrometer output 166 may be preferably used to provide both an indication of malfunction (such as the obstruction blockage 156), and to suppress erroneous measurement outputs from the measuring device 180 when such malfunctions occur. For example, the electrometer output 166 may be used to cause the operation of a warning light, or to cause a warning message to appear on a CRT screen. Also, the electrometer output 166 may be used by equipment in a system (such as the data system 198) to suppress an electrical measurement output when malfunctions are detected.

Figure 8:
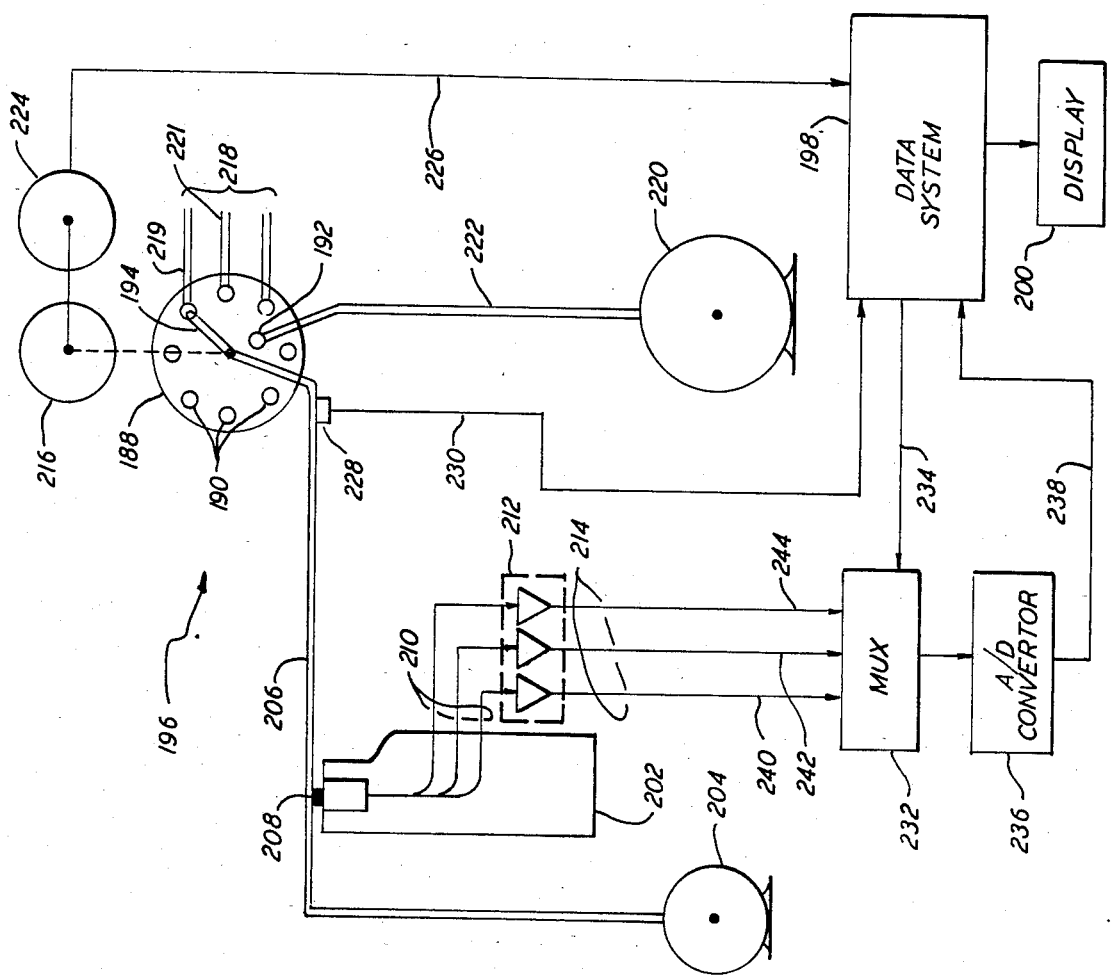
FIG. 8 is an electrical block diagram for the gas collection system using a multi-port selector valve.

Referring next to FIG. 8, an alternative to the gas collection system 114 of FIG. 4 is shown which utilizes a sampled data method to shorten the time required to sample gases from all the inlet ports. A multi-port selector valve 188 is shown symbolically as having eight inlet ports 190 and operates to selectively couple each of the inlet ports 190 to either an outlet port 192 or a sample tube 194. The valve 188 is preferably constructed so that the distances between the inlet ports 190 are as small as possible; being only large enough to prevent undesired gases from being ingested by the sample tube 194 while the sample tube 194 is withdrawing gases from a selected port. In addition to the multi-port valve 188, the sampling system 196 of FIG. 8 includes a data system 198 having a display 200 connected thereto. The data system 198 may be a conventional, commercially available process control computer. In the sampling system 196, the multi-port valve 118 of FIGS. 5-7 may be substituted for the multi-port valve 188. Alternatively, the valve 10 of FIGS. 1-4 may be substituted for the valve 188.

The sample tube 194 is connected to a measuring device 202 which may be a mass spectrometer for determining the composition of gases received from the sample tube 194. Such a mass spectrometer would preferably use a small volume ion source (not shown) to reduce the source time constant to a few milliseconds. The sample tube 194 is connected to a vacuum pump 204 by a pump line 206. The purpose of vacuum pump 204 is to withdraw sample gases from the valve 188 through the sample tube 194. A leak valve 208 is positioned midway in the length of the pump line 206 in order to allow a small amount of gas from the line 206 to be drawn into the measuring device 202. The measuring device 202 may be a mass spectrometer which has a plurality of spectrometer collector outputs 210 for the constituent gases of interest, and which are provided in parallel to a plurality of fast response electrometer amplifiers 212 in order to produce a plurality of parallel amplified outputs 214. The amplified outputs 214 are provided on the signal lines 240, 242, and 244 to a multiplexer 232.

A motor 216 is used as described above (in reference to valve 10 or valve 118) to move the sample tube 194 between each of the inlet ports 190 in order to select which of a plurality of gas inlet tubes 218 that gases will be sampled from. The motor 216 may be of the stepper type or of the continuously rotating type. Inlet tubes 219 and 221 are representative of the group of eight inlet tubes 218 which are coupled to respective ones of the inlet ports 190. A vacuum pump 220 is connected to the outlet port 192 by a pump line 220 in order to withdraw gases from inside the multi-port valve 188. A position detector 224 such as a shaft decoder coupled to the motor 216 is used in order to detect the position of the sample tube 194 with respect to the inlet ports 190, and produces a position indication signal on the signal line 226. A blockage detector 228 may be connected to the pump line 206 in order to detect blockage of fluids flowing through the inlet tubes 218, and in order to produce an indication of such blockage on the signal line 230. It is preferable that the blockage detector 228 be constructed as shown in FIG. 7 using the ionization source 160, detector plate 162, and electrometer 164. The data system 198 receives the signal lines 226 and 230 as inputs in order to control the operation of a multiplexer 232 through a signal line 234. A function of the data system 198 is to enable the multiplexer 232 through the signal line 234 when signals on the signal line 226 indicate that the sample tube 194 is properly aligned with selected ones of the inlet ports 190. An analog to digital converter 236 is connected to the output of the multiplexer 232 in order to produce digital output signals on the signal line 238 which is connected as an input to the data system 198. The function of the analog to digital convertor 236 is to create digital signals representative of the analog signals received from the amplified outputs 214 when the multiplexer 232 is enabled by the signal line 234. The data system 198 provides an output to the display 200 in order to display data concerning the measurements made by the measuring device 202, such as displays of gas constituent concentrations measured by a mass spectrometer. The data system 198 may also produce an indication on the display 200 when the signal line 230 indicates that a flow blockage has occurred, and the data system 198 may avoid the processing of measurement data from the multiplexer 232 and convertor 236 for measurements relating whichever of the inlet tubes 218 has been blocked.

The multi-port valve 188 is preferably constructed similarly to the multi-port valve 118 of FIGS. 5-7 in order to insure reliable operation for high speed sampling when the motor 216 is operated at high speeds. One application of the sampling system 196 is for the measurement of the inspired and expired breath of up to eight human medical patients in an intensive care unit (ICU). A relatively fast sampling rate may be used for the gases in order to obtain multiple measurements using the measurement device 202 from each of the patients during each patient's inhalation and exhalation respiration cycle. For such a respiration gas sampling system, the sample tube 194 is preferably rotated at approximately 900 rotations per minute. The inlet ports 190 preferably each have the same diameter, and are spaced apart by a distance equal to such diameter. Such a construction will cause gases from each of the ports 190 to be sampled during sampling periods of approximately 4 milliseconds duration, and will produce a rotational period of approximately 67 milliseconds for the sample tube 194. This construction would allow gases from each of the inlet tubes 218 to be sampled once each in an interval of 67 milliseconds. It is preferable that the sampling period for each of the inlet ports 190 be at least approximately 4 milliseconds for each sample to accommodate the settling time of the measurement device 202.

During the high speed rotation of the sample tube 194 by the motor 216, the position detector 224 (which may be a shaft decoder 138 as shown in FIG. 5) produces electrical signals on the signal line 226 indicating the instantaneous position for the sample tube 194 so that the correspondence between the gas samples inside the sample tube 194 and the particular inlet port of the ports 190 from which the gas was received may be determined by the data system 198. The function of the multiplexer 232 is to insure that measurements are obtained from the measuring device 202 only at such times as when the sample tube is aligned with an individual inlet port 190 and to avoid the making of measurements during the time that the sample tube 194 is between adjacent ones of the inlet ports 190.

Figure 9:
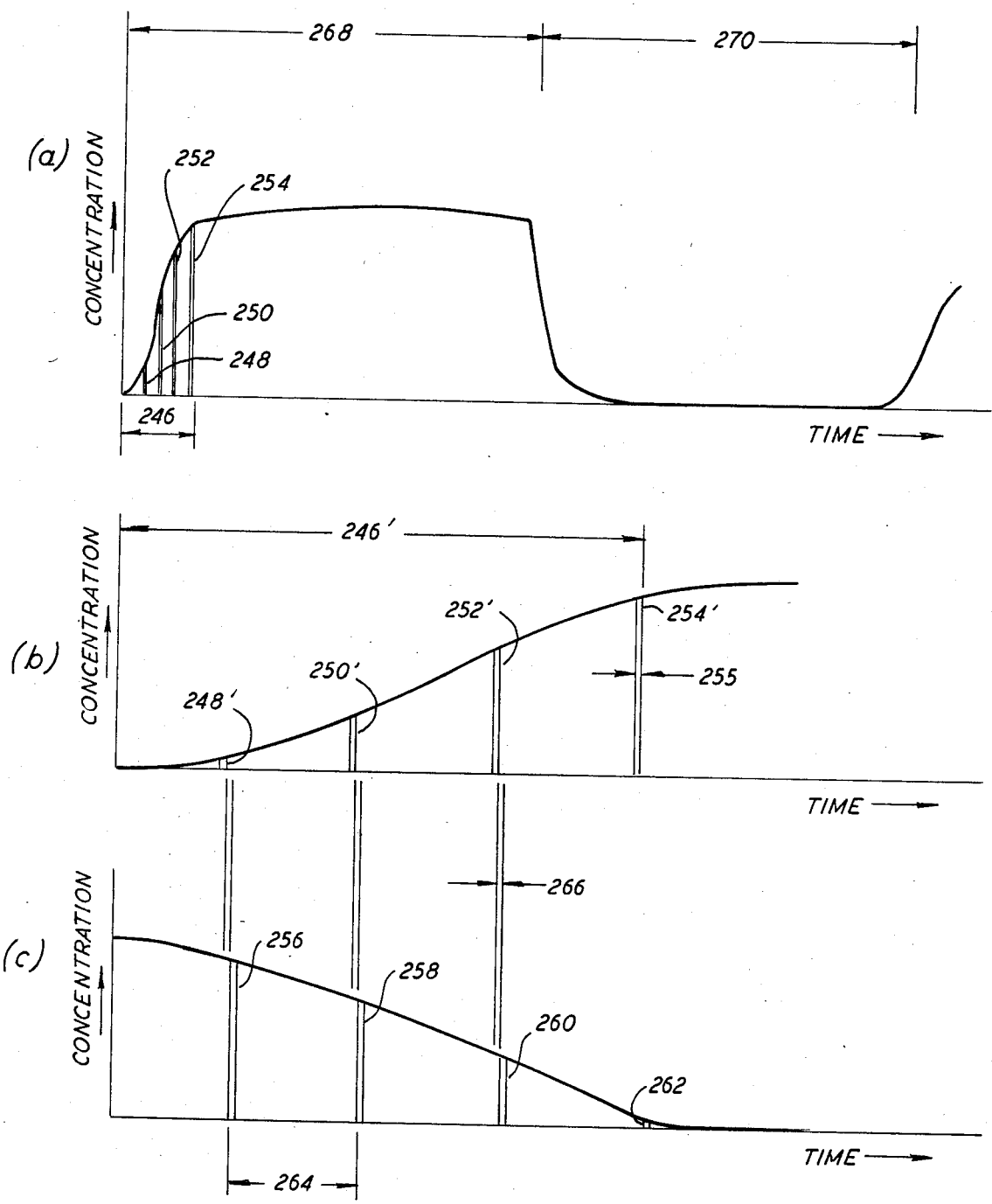
FIG. 9 is a set of three gas concentration versus time waveforms showing the sampling of fluids used in the system of FIG. 8.

Referring next to FIG. 9, the waveforms (a), (b), and (c) are gas concentration versus time waveforms for gases present in the inlet tubes 218. Overlaid on the waveforms of FIG. 9 are sample period marker lines indicating the times when the multiplexer 232 is enabled by the data system 198. The waveforms of FIG. 9 show typical waveforms expected for concentration of a gas being supplied to medical patients for respiration.

For purposes of explanation, the waveform (a) represents the concentration of a constituent gas in the gases received from inlet tube 219. The multiplexer 232 is enabled by the data system 198 during sampling periods 248, 250, 252, and 254 during the time duration 246 in order to collect measurements from the amplified output 240 corresponding to the concentration of that constituent gas. The vertical lines for sampling periods 248, 250, 252 and 254 indicate the times when the sample tube 194 is positioned to receive gas samples from the inlet tube 219, and also indicate times when the multiplexer 232 is enabled by the data system 198. The waveform (a) of FIG. 9 is divided into an inhalation time period 268 when the concentration of the constituent gas is high in inlet tube 219 and an exhalation time period 270 when the concentration of the constituent gas is low in inlet tube 219.

The waveform (b) of FIG. 9 is the same as the waveform (a) of FIG. 9, but with an expanded time scale such that the time duration 246 is expanded to 246' for purposes of illustration. The time duration 246 and 246' are approximately equal to 276 milliseconds. The length 255 of the sampling period 254' is approximately 4 milliseconds. The length of each of the sampling periods 248', 250', 252' and 254' is approximately the same.

Waveform (c) shows the concentration of the constituent gas in gases received from the inlet tube 221 of FIG. 8 and has the same time scale as the waveform (b). The sampling periods 256, 258, 260, and 262 follow the sampling periods 248', 250', 252', and 254', respectively. The sampling interval between sequential sampling periods for the same inlet tube is approximately 67 milliseconds, as is illustrated by the sampling interval 264 between sampling periods 256 and 258 for inlet tube 221. A sampling interval of 67 milliseconds allows a human respiration waveform to be reconstructed with reasonable fidelity using conventional low pass filtering techniques. A delay time 266 of approximately 4 milliseconds is the time when the multiplexer 232 is selectively disabled between sequential samples from the inlet tubes 218 so that measurements by the measuring device 202 are not considered during the time that the sample tube 194 is between adjacent ones of the inlet ports 190. The use of the delay time 266 insures that errors are not produced by the measurement of mixed gases obtained from more than one of the inlet ports 190.

It is possible that various alternative constructions and operating techniques may be used for the multi-port valve and gas collection and sampling system of this invention. While this description does present the preferred embodiment, it is possible that equivalent constructions may exist without departing from the spirit of the invention, the scope of which is defined by the following claims.

What is claimed is:

1. A multi-port valve comprising:
a valve body;
a plurality of means for channeling gases into said valve body;
means for intercepting gases from said plurality of means for channeling, said means for intercepting having an entrance opening which is movable to select between each of said means for channeling, by moving said opening to intercept gases substantially exclusively from said selected means for channeling, said means for intercepting having an outlet for said intercepted gases;
means for moving said means for intercepting into selective alignment with each of said plurality of means for channeling to intercept gases therefrom;
wherein said means for channeling comprise inlet ports in said valve body;
wherein said means for intercepting gases comprises a sample tube pivotably mounted inside said valve body to move between said inlet ports;
wherein said means for moving comprises:
 a sample tube guide mounted in said valve body and coupled to move said sample tube; and
 means for actuating said sample tube guide;
a position detector for detecting the position of said sample tube guide and to indicate the alignment of said sample tube with each of said inlet ports; and
wherein said sample guide has a magnet attached thereto, and wherein said position detector comprises a plurality of magnetic field detecting Hall effect devices positioned on said valve body to detect the position of said magnet.

2. A multi-port valve comprising:
a valve body having an inlet fitting block and a vacuum housing secured thereto to define a manifold space inside said valve body, said inlet fitting block having a plurality of inlet ports, said inlet ports comprising fluid passages through said inlet fitting block, said inlet ports being arranged side-by-side around said inlet fitting block;
a sample tube mounted inside said manifold space, said sample tube having a tube entrance end for receiving fluids, said sample tube being positionable to allow said tube entrance end to move between said inlet ports in order to select an inlet port, said tube entrance end being spaced away from said inlet fitting block by a distance large enough to allow fluid from the selected inlet port to both flow past and flow into said tube entrance end;
a guide rotor mounted for rotation inside said manifold space, said guide rotor being operatively connected to said sample tube so that said sample tube entrance end moves between said inlet ports as said guide rotor is rotated;
a motor coupled to said guide rotor for rotating said guide rotor;

a magnetic coupled between said motor and said guide rotor, said magnetic coupling comprising:
an input rotor attached to said motor outside said valve body; and
a magnetic follower attached to said guide rotor inside said valve body and magnetically coupled to said input rotor through said valve body, so that rotational torque from said motor is transmitted from said input rotor to said magnetic follower for rotating said guide rotor.

3. A multi-port valve comprising:
a valve body having an inlet fitting block and a vacuum housing secured thereto to define a manifold space inside said valve body, said inlet fitting block having a plurality of inlet ports, said inlet ports comprising fluid passages through said inlet fitting block, said inlet ports being arranged side-by-side around said inlet fitting block;
a sample tube mounted inside said manifold space, said sample tube having a tube entrance end for receiving fluids, said sample tube being positionable to allow said tube entrance end to move between said inlet ports in order to select an inlet port, said tube entrance end being spaced away from said inlet fitting block by a distance large enough to allow fluid from the selected inlet port to both flow past and flow into said tube entrance end;
a guide rotor mounted for rotation inside said manifold space, said guide rotor being operatively connected to said sample tube so that said sample tube entrance end moves between said inlet ports as said guide rotor is rotated;
a motor coupled to said guide rotor for rotating said guide rotor; and
a gas tight feedthrough coupler mounted through said valve body, connected to said guide rotor inside said valve body, and connected to said motor outside said valve body, so that rotational torque from said motor is transmitted through said coupler for rotating said guide rotor.

4. A multi-port valve comprising:
a valve body having an inlet fitting block and a vacuum housing secured thereto to define a manifold space inside said valve body, said inlet fitting block having a plurality of inlet ports, said inlet ports comprising fluid passages through said inlet fitting block, said inlet ports being arranged side-by-side around said inlet fitting block;
a sample tube mounted inside said manifold space, said sample tube having a tube entrance end for receiving fluids, said sample tube being positionable to allow said tube entrance end to move between said inlet ports in order to select an inlet port, said tube entrance end being spaced away from said inlet fitting block by a distance large enough to allow fluid from the selected inlet port to both flow past and flow into said tube entrance end;
a guide rotor mounted for rotation inside said manifold space, said guide rotor being operatively connected to said sample tube so that said sample tube entrance end moves between said inlet ports as said guide rotor is rotated;
a motor coupled to said guide rotor for rotating said guide rotor;
a blockage detector for detecting the blockage of gases flowing into said inlet ports, said blockage detector comprising:
an ionizing radiation source mounted on said sample tube entrance end for ionizing gases inside said manifold space;
a detector plate mounted inside said sample tube for collecting electrical charge from ionized gases flowing inside said sample tube; and
an electrometer for detecting the accumulation of electrical charge on said detector plate and producing an indication of inlet port blockage in response thereto.

5. A multi-port valve comprising:
a valve body having an inlet fitting block and a vacuum housing secured thereto to define a manifold space inside said valve body, said inlet fitting block having a plurality of inlet ports, said inlet ports comprising fluid passages through said inlet fitting block, said inlet ports being arranged side-by-side around said inlet fitting block;
a sample tube mounted inside said manifold space, said sample tube having a tube entrance end for receiving fluids, said sample tube being positionable to allow said tube entrance end to move between said inlet ports in order to select an inlet port, said tube entrance end being spaced away from said inlet fitting block by a distance large enough to allow fluid from the selected inlet port to both flow past and flow into said tube entrance end;
a guide rotor mounted for rotation inside said manifold space, said guide rotor being operatively connected to said sample tube so that said sample tube entrance end moves between said inlet ports as said guide rotor is rotated;
a motor coupled to said guide rotor for rotating said guide rotor;
a position detector for detecting the position of said guide rotor;
wherein said position detector comprises:
a magnet attached to sid guide rotor inside said valve body; and
a plurality of Hall-effect magnetic detectors positioned around said valve body to respond to the position of said magnet and to indicate the position of said guide rotor.

6. A gas collection system for collecting gases from a plurality of inlet tubes to provide a gas sample through a sample tube, said system comprising:
a vacuum pump;
a multi-port valve connected to receive gases from each of said inlet tubes through separate inlet ports, said valve having an internal manifold space into which said inlet ports are connected, said manifold space being connected to said vacuum pump, said vacuum pump operating to pump gases from said manifold space at a rate sufficient so that the volumetric flow rate through each of said inlet ports into said manifold space is greater than a first volumetric flow rate;
said valve further comprising a pivoting sample tube inside said manifold space and a movable tube guide for selectively positioning an open end of said sample tube adjacent to said inlet ports to receive sample gases therefrom and to transfer gas samples outside of said valve, said valve further comprising an actuator for moving said tube guide and a position detector for detecting the position of said tube guide and said sample tube;
a valve controller having an input connected to said position detector and having an output connected to control said actuator by causing said actuator to move said sample tube guide until said position detector indicates that said sample tube is positioned correctly with respect to the selected inlet port; and
wherein said controller operates to selectively skip over the sampling of gases from preselected inlet tubes.

7. A gas collection system for collecting gases from a plurality of inlet tubes to provide a gas sample through a sample tube, said system comprising:

a vacuum pump;
a multi-port valve connected to receive gases from each of said inlet tubes through separate inlet ports, said valve having an internal manifold space into which said inlet ports are connected, said manifold space being connected to said vacuum pump, said vacuum pump operating to pump gases from said manifold space at a rate sufficient so that the volumetric flow rate through each of said inlet ports into said manifold space is greater than a first volumetric flow rate;
said valve further comprising a pivoting sample tube inside said manifold space and a movable tube guide for selectively positioning an open end of said sample tube adjacent to said inlet ports to receive sample gases therefrom and to transfer gas samples outside of said valve, said valve further comprising an actuator for moving said tube guide and a position detector for detecting the position of said tube guide and said sample tube;
a valve controller having an input connected to said position detector and having an output connected to control said actuator by causing said actuator to move said sample tube guide until said position detector indicates that said sample tube is positioned correctly with respect to the selected inlet port; and
a blockage detector for detecting the blockage of flow through said inlet ports to indicate the presence of contamination in said gas samples.

8. A gas sampling system for collecting gas samples from a plurality of gas inlet tubes, said system comprising:

a vacuum pump;
a multi-port valve having inlet ports for connection of said plurality of gas inlet tubes, a sampling tube which moves continuously between said inlet ports to selectively intercept gas flowing therefrom as gas flows over said sampling tube, an outlet port in said valve coupled to said vacuum pump for removing gases flowing inside said valve from said gas inlet ports, and a position detector for detecting the position of said sample tube;
a measuring device coupled to said sample tube for continuously measuring the gas flowing therefrom and producing a measurement output;
a data system having an input coupled to receive said measurement output and responsive to said position detector for indicating the measurements of the gas provided by said gas inlet ports; and
a blockage detector for detecting the blockage of flow through said inlet ports, and wherein said data system is responsive to said blockage detector to inhibit the indication of measurements when contamination is present in said gas samples.

9. A method of collecting gases to provide sampled gas in sample tube from a plurality of inlet ports which are connected to a common manifold, the method comprising the steps of:

continuously withdrawing gases from inlet ports into said manifold, with gases being drawn from each inlet port at a rate greater than a first volumetric rate;
withdrawing gases into said sample tube at a second volumetric rate less than said first volumetric rate;
moving said sample tube to each inlet port to receive said sampled gas therefrom unmixed with gases from said manifold;
ionizing the gases in said manifold; and
detecting the presence of ionization in gases passing through said sample tube to detect the blockage of gas flow through said input ports.

* * * * *